US012685501B2

(12) United States Patent (10) Patent No.: US 12,685,501 B2
Cantrell et al. (45) Date of Patent: Jul. 21, 2026

(54) MASKLESS 2D/3D ARTIFICIAL SUBTRACTION ANGIOGRAPHY

(71) Applicants: Northwestern University, Evanston, IL (US); Ann and Robert H. Lurie Children's Hospital of Chicago, Chicago, IL (US)

(72) Inventors: Donald R. Cantrell, Chicago, IL (US); Sameer A. Ansari, Chicago, IL (US); Leon Cho, Chicago, IL (US)

(73) Assignees: Northwestern University, Evanston, IL (US); Ann and Robert H. Lurie Children's Hospital of Chicago, Chicago, IL (US)

( * ) Notice: Subject to any disclaimer, the term of this patent is extended or adjusted under 35 U.S.C. 154(b) by 657 days.

(21) Appl. No.: 18/010,347

(22) PCT Filed: Jun. 17, 2021

(86) PCT No.: PCT/US2021/037936

§ 371 (c)(1),
(2) Date: Dec. 14, 2022

(87) PCT Pub. No.: WO2021/257906

PCT Pub. Date: Dec. 23, 2021

(65) Prior Publication Data

US 2023/0263493 A1 Aug. 24, 2023

Related U.S. Application Data

(60) Provisional application No. 63/040,271, filed on Jun. 17, 2020.

(51) Int. Cl.
G06K 9/00 (2022.01)
A61B 6/50 (2024.01)
(Continued)

(52) U.S. Cl.
CPC ............ A61B 6/504 (2013.01); G06T 7/0012 (2013.01); G06T 15/00 (2013.01); G06V 10/44 (2022.01);
(Continued)

(58) Field of Classification Search
None
See application file for complete search history.

(56) References Cited

U.S. PATENT DOCUMENTS

2014/0073976 A1    3/2014  Fonte et al.
2014/0270437 A1    9/2014  Shreiber et al.
(Continued)

OTHER PUBLICATIONS

David G. Lowe, "Distinctive Image Features from Scale-Invariant Keypoints" Computer Science Department University of British Columbia visited on Jun. 10, 2021 at https//www.cs.ubu.ca/-lowe. papers/ijcv04.pdf pp. 1-28.
(Continued)

*Primary Examiner* — Sj Park
(74) *Attorney, Agent, or Firm* — Banner & Witcoff, Ltd.

(57) ABSTRACT

During catheter-based angiography, the bone and soft tissues degrade visualization of the vasculature, which is of primary interest in such medical imaging procedures. The present disclosure includes systems and methods utilizing a trained neural network to remove the bone and soft tissue densities from post-contrast images, revealing isolated vascular densities, without the need for a standard pre-injection digital mask and in the setting of patient motion. The final angiographic images may be created in real-time. Systems and methods for the training and optimization of the disclosed neural network are also described.

18 Claims, 7 Drawing Sheets

(51) Int. Cl.

| | | |
|---|---|---|
| *G06T 7/00* | (2017.01) | |
| *G06T 15/00* | (2011.01) | |
| *G06V 10/44* | (2022.01) | |
| *G06V 10/74* | (2022.01) | |
| *H04N 5/14* | (2006.01) | |

(52) U.S. Cl.
CPC ........... *G06V 10/761* (2022.01); *H04N 5/145* (2013.01); *G06T 2207/10081* (2013.01); *G06T 2207/10088* (2013.01); *G06T 2207/30101* (2013.01)

(56) References Cited

U.S. PATENT DOCUMENTS

| | | | |
|---|---|---|---|
| 2016/0135775 A1* | 5/2016 | Mistretta | .............. G06T 7/0012 |
| | | | 600/419 |
| 2016/0328855 A1* | 11/2016 | Lay | ........................... G06T 7/11 |
| 2018/0055355 A1 | 3/2018 | Sarunic et al. | |
| 2019/0180438 A1* | 6/2019 | Buckler | ................ G06T 7/0012 |
| 2019/0287239 A1* | 9/2019 | Nett | ........................ G16H 50/20 |
| 2019/0304592 A1 | 10/2019 | Ma et al. | |
| 2020/0085394 A1* | 3/2020 | Turcea | ................... A61B 5/352 |

OTHER PUBLICATIONS

Yufeng Gao et al., "Deep Learning-based Digital Subtraction Angiography Image Gneration" International Journal of Computer Assisted Radiology and Surgery (2019) 14: 1775-1784 visited on Jun. 10, 2021 https://doi.org/10.1007/s11548-019-02040-x.

Daiju Ueda et al., "Deep Learning-based Angiogram Generation Model for Cerebral Angiography without Misregistration Artifacts" Radiology 2021; 299:675-681 visited on Jun. 10, 2021 http://doi.org/10.1148/radiol.2021203692.

Oct. 6, 2021—(WO) International Search Report and Written Opinion—App PCT/US2021/037936.

* cited by examiner

100

130

Server System

150

Deep Learning
Neural Network

140

110
Client Devices

120

Mobile Device

200

Computing Device

215

Memory

203 — Processor

217

Operating System

221

Database

205 — RAM

207 — ROM

Applications

219

209 — Input/Output Device

Communication Interface — 211

300

MASKLESS 2D/3D ARTIFICIAL SUBTRACTION ANGIOGRAPHY

RELATED APPLICATION DATA

This application is a U.S. National Stage application under 35 U.S.C. § 371 of International Application PCT/US2021/037936, filed Jun. 17, 2021, which claims priority to U.S. Provisional Patent Application No. 63/040,271, filed Jun. 17, 2020, and entitled "Maskless 2d/3d Artificial Subtraction Angiography," the disclosures of which are incorporated herein by reference in their entirety for any and all non-limiting purposes.

BACKGROUND

The present disclosure relates generally to medical imaging techniques. More specifically, the present disclosure relates to systems and methods for conducting medical angiography in individuals without utilizing digital subtraction techniques to improve images. The present systems and methods disclosed herein utilize a novel algorithm and machine learning techniques to enhance images.

Conventional digital subtraction angiography (DSA) is a fluoroscopic technique used extensively in interventional radiology for visualizing blood vessels. Radiopaque structures, however, such as bones and other tissues are subtracted digitally from the desired images to allow for a more accurate depiction of the blood vessels. The final images are created using a contrast medium by subtracting a pre-contrast image (i.e., a "mask") from subsequent images once the contrast medium has been introduced into a structure. In traditional prior art systems, images are acquired by exposing an area of interest with time-controlled X-rays while injecting a contrast medium into the blood vessels. The image obtained includes the blood vessels, together with all overlying and underlying structures, such as bone and muscle. The images are useful for determining anatomical position and variations, but unhelpful for visualizing blood vessels accurately. To remove the distracting structures to see the blood vessels better, a mask image is acquired. The mask image is simply an image of the same area prior to administration of contrast. Conventional radiological equipment is used to capture the image to produce a set of images of the same area over a specific time period. Each subsequent image gets the original mask image subtracted out. Generally, a radiologist will control how much contrast media is required. Generated images typically appear with a pale grey background, which produces a high contrast to the blood vessels, which typically appear dark grey. The images are computer generated in real-time while the radiologist injects contrast into the blood vessels.

Conventional methods, however, are severely impacted by motion that occurs between the acquisition of the mask and subsequent images. For example, voluntary, respiratory, or cardiac motion can all degrade vascular imaging with the digital subtraction technique. Additionally, the acquisition of a mask or "mask frame" increases radiation exposure to the patient and staff, particularly during rotational angiography, which requires many X-ray projections to compute 3D reconstructions, substantially increasing the radiation dose. The goal of the present systems and methods disclosed herein is to eliminate such problems by using a novel, deep-learning algorithm (i.e., a machine learning model) that can perform vessel segmentation and/or computational isolation of vascular contrast enhancement on raw angiographic images to mitigate and/or overcome the degrading effects of motion on the final image. The systems and methods disclosed herein also minimize radiation dose exposure to both patients and medical staff.

SUMMARY

Catheter-based DSA techniques have traditionally relied upon mask-based subtraction methods to remove bone and soft tissue densities and enable better visualization of the underlying vessels. But such techniques are prone to suboptimal quality related to interval cardiac/respiratory or other voluntary patient motion. Disclosed herein are systems and methods for utilizing machine learning technologies that can isolate vascular enhancement from bone and soft tissue densities without a pre-injection mask. These new systems and methods for maskless artificial subtraction angiography can decrease the radiation doses administered to the patient, and even more importantly, are resistant to these motion artifacts by allowing automatic subtraction of each image via a dynamic machine learning algorithm rather than a static pre-injection mask. The systems and methods can be applied to both 2D and 3D rotational angiography, and may also be applied to enhance vessel segmentation techniques of noninvasive computed tomography (CT) and magnetic resonance (MR) angiography via transfer learning.

Example applications may include bone and soft tissue removal during 3D rotational catheter angiography, bone and soft tissue removal during 2D catheter angiography, bone and soft tissue removal during 2D or 3D catheter angiography in the setting of motion, which may be due to voluntary patient movement, respiratory movement, or cardiac movement, and vessel segmentation and/or isolated vascular enhancement in CT or MR angiography.

The present disclosure may utilize a variant of the U-net deep learning neural network architecture to segment vessels from 2D and 3D angiographic images. Initial training of the neural network is performed utilizing the large database of historical mask-based 2D and 3D digital subtractions available in a picture archiving and communication system (PACS), which provide immediate input-target pairs for neural network optimization. Data augmentation with the addition of artificial motion is utilized to optimize vessel segmentation in the setting of cardiac, respiratory, and voluntary patient motion.

The systems and methods disclosed herein significantly improve vascular imaging during catheter-based angiography of the brain, the heart, and the remainder of the body by avoiding the artifacts that result from cardiac, respiratory, or voluntary patient motion in current mask-based subtraction techniques. The novel maskless subtraction angiography technique may enable soft tissue and bone subtraction in areas previously limited by substantial motion, such as cardiac imaging (coronary angiography). Additionally, the systems and methods disclosed herein, via the novel algorithm, utilize transfer-learning technology/machine learning to transform real-time imaging of the blood vessels into extremely useful computer generated images critical to patient care to include disease diagnosis and treatment. The methods and systems disclosed herein may also improve current vessel segmentation techniques employed in noninvasive imaging such as CT/MR angiography, which are suboptimal using manual threshold and maximum intensity projection techniques utilized in prior art systems. The systems and methods disclosed herein may also perform computational isolation of vascular contrast enhancement techniques in angiograms to improve vascular imaging.

In one aspect, an embodiment of the present disclosure provides a method for maskless angiography that may include obtaining an angiographic image from an individual, obtaining a subset of data that is extracted from historical angiograms that identify patient motion. In some examples, the method may include generating artificial motion based upon the subset of data. In other examples, an artificial motion-augmented subset of data may be used to train a deep learning model to generate a final angiographic image in which bone and soft tissue densities have been removed. In some examples, the method is conducted in real-time.

In another aspect, a system for maskless angiography disclosed herein may include an angiographic imaging device configured to generate an angiographic image from an individual, a processing device configured to obtain a subset of data extracted from historical angiograms. In some cases, the subset of data may identify patient motion. In other cases, the processing device may generate artificial motion based upon the subset of data. In other cases, the generated artificial motion may be used to create motion-augmented data sets to train a deep learning model to generate an angiographic image in which bone and soft tissue densities have been removed. In other cases, the processing device may generate a final angiographic image.

In still other aspects, one or more non-transitory computer-readable media is disclosed herein having instructions stored thereon, when executed, cause at least one processing device to obtain a subset of data extracted from historical angiograms and identifying patient motion, generate artificial motion based upon the subset of data, generate a motion-augmented dataset that can be used to train a machine learning algorithm to isolate vascular densities from raw angiograms, and generate a final angiographic image.

In other aspects, a method of generating a maskless artificial subtraction angiography image using a machine learning model disclosed herein may include the steps of obtaining raw angiographic images from an individual or patient. The raw angiographic images may be three-dimensional, spatiotemporal, multi-frame angiographic inputs with two spatial dimensions and one temporal dimension. In certain other examples, the raw angiographic images may consist of three spatial dimensions. The method may include utilizing the spatial and temporal information in the raw angiographic input images to identify vascular densities, and then generating a final three-dimensional spatiotemporal angiographic image with bone and soft tissue structures removed from the final angiographic image, leaving isolated vascular densities. In another example, the machine learning model may be trained and optimized by a method including the steps of obtaining a database of raw angiographic images from many individuals or patients in which the raw angiographic images are three-dimensional, spatiotemporal, multi-frame angiographic inputs. Motion estimates may then be calculated using the database of raw angiographic images, isolating motionless angiographic images from the database, transforming the motionless raw angiographic images into digital subtraction angiography images to generate input-output data pairs, applying the motion estimates to the input-output data pairs, and utilizing the data pairs for training and optimizing the machine learning model for the generation of maskless artificial subtraction angiography images.

In some examples, the angiographic images may be generated in real-time or near real-time. In other examples, the raw angiographic images are obtained at a rate of about 1 to about 16 frames per second. In some examples, the raw angiographic images are obtained at a rate of at least 16 frames per second. In still other examples, the raw angiographic images are obtained at a rate of at least 20 frames per second. In certain examples, the spatiotemporal data pairs are augmented with real motion data, augmented motion data, and/or artificial motion data. In another example, the method may further include the steps of identifying a plurality of known anatomical features in the raw angiographic images from at least one individual, matching the plurality of known anatomical features in a historical motion-degraded dataset to compute an interframe motion, and the motion estimates may include the interframe motion, and applying the interframe motion to the motionless dataset to obtain high quality input raw angiography-output digital subtraction angiography data pairs. In certain examples, the interframe motion may be further augmented with additional artificial motion prior to application to the motionless dataset for the generation of a motion-augmented data pair. In other examples, the raw angiographic images are obtained from the head or neck of the individual, the torso of the individual, an appendage of the individual, or combinations thereof. In yet other examples, the raw images are obtained from a three-dimensional rotational angiographic imaging device, MRI device, or CT device in which the three-dimensional data consists of three spatial dimensions instead of two spatial dimension and one temporal dimension.

In an alternative aspect, a system for generating a maskless artificial subtraction angiography image disclosed herein may include an angiographic imaging device configured to generate raw angiographic images from an individual, a machine learning model configured to remove bone and soft tissue densities and isolate vascular densities, and a processing device configured to generate a final angiographic image in real-time or near real-time in which bone structures may be removed from the final angiographic image. In some examples, the raw angiographic images may be three-dimensional, spatiotemporal, multi-frame angiographic inputs, such as inputs consisting of two spatial dimensions and one temporal dimension. In other examples, the raw angiographic images may consist of three spatial dimensions. In other examples, the machine learning model may include three-dimensional, spatiotemporal information from at least 10,000 historical angiographic datasets. In still other examples, the datasets may further include three-dimensional rotational angiographic imaging device data, MRI device data, and/or CT device data, and the three-dimensional data may consist of three spatial dimensions in place of inputs consisting of two spatial dimensions and one temporal dimension.

In other examples, the machine learning model may be further configured to compute motion estimates that may be generated from a motion degraded dataset. In another example, the raw angiographic images may include a plurality of known anatomic features that may be identified on a series of temporal angiographic frames, and the plurality of known anatomic features may be matched across frames to measure interframe motion. In other examples, the raw angiographic images may be images of the head or neck of the individual, the torso of the individual, an appendage of the individual, or combinations thereof.

In still another aspect, a method of angiographic motion stabilization in artificial subtraction angiography is disclosed including the steps of comprising collecting a plurality of raw angiographic images that may be three-dimensional, spatiotemporal, and multi-frame angiographic inputs rather than images consisting of two spatial dimensions and one temporal dimension, matching known anatomical features from the plurality of raw angiographic images, computing interframe motion from matched anatomical features, computing a motion-stabilized series of angiographic images using the computed interframe motion, and generating a digital subtraction angiography from the motion-stabilized dataset in which the bone structures may be removed from the final angiographic image. In certain examples, the method disclosed herein may further include the steps of obtaining raw angiographic images from an individual, matching the plurality of known anatomic features of the raw angiographic images from the individual across the series of temporal angiographic frames, computing a measure of interframe motion using the matched plurality of known anatomic features, generating a motion-stabilized dataset using the interframe motion, performing digital subtraction angiography on the motion-stabilized series of angiographic images stabilized with plurality of known anatomic features of the raw angiographic images from the individual, and generating a final angiographic image in which the bone structures are removed from the final angiographic image, and generating the final angiographic image in real-time or near real-time.

The systems and methods disclosed herein significantly improve vascular imaging during catheter-based angiography of the brain, the heart, and the remainder of the body by avoiding the artifacts that result from cardiac, respiratory, or voluntary patient motion and are resistant to current mask-based subtraction techniques. The novel maskless subtraction angiography techniques and the novel computational isolation of vascular contrast enhancement techniques may enable soft tissue and bone subtraction in areas previously limited by substantial motion, such as cardiac imaging (coronary angiography). Additionally, the systems and methods disclosed herein utilize transfer learning technologies and may also improve current vessel segmentation techniques employed in noninvasive imaging such as CT/MR angiography, which are suboptimal using manual threshold and maximum intensity projection techniques utilized in prior art systems.

Additional aspects, advantages, features and objects of the present disclosure may be made apparent from the drawings and the detailed description of the illustrative embodiments construed in conjunction with the appended claims that follow. It will be appreciated that features of the present disclosure are susceptible to being combined in various combinations without departing from the scope of the present disclosure as defined by the appended claims.

BRIEF DESCRIPTION OF THE DRAWINGS

The present disclosure is illustrated by way of example and not limited in the accompanying figures in which like reference numerals indicate similar elements and in which.

DETAILED DESCRIPTION

Figure 1:
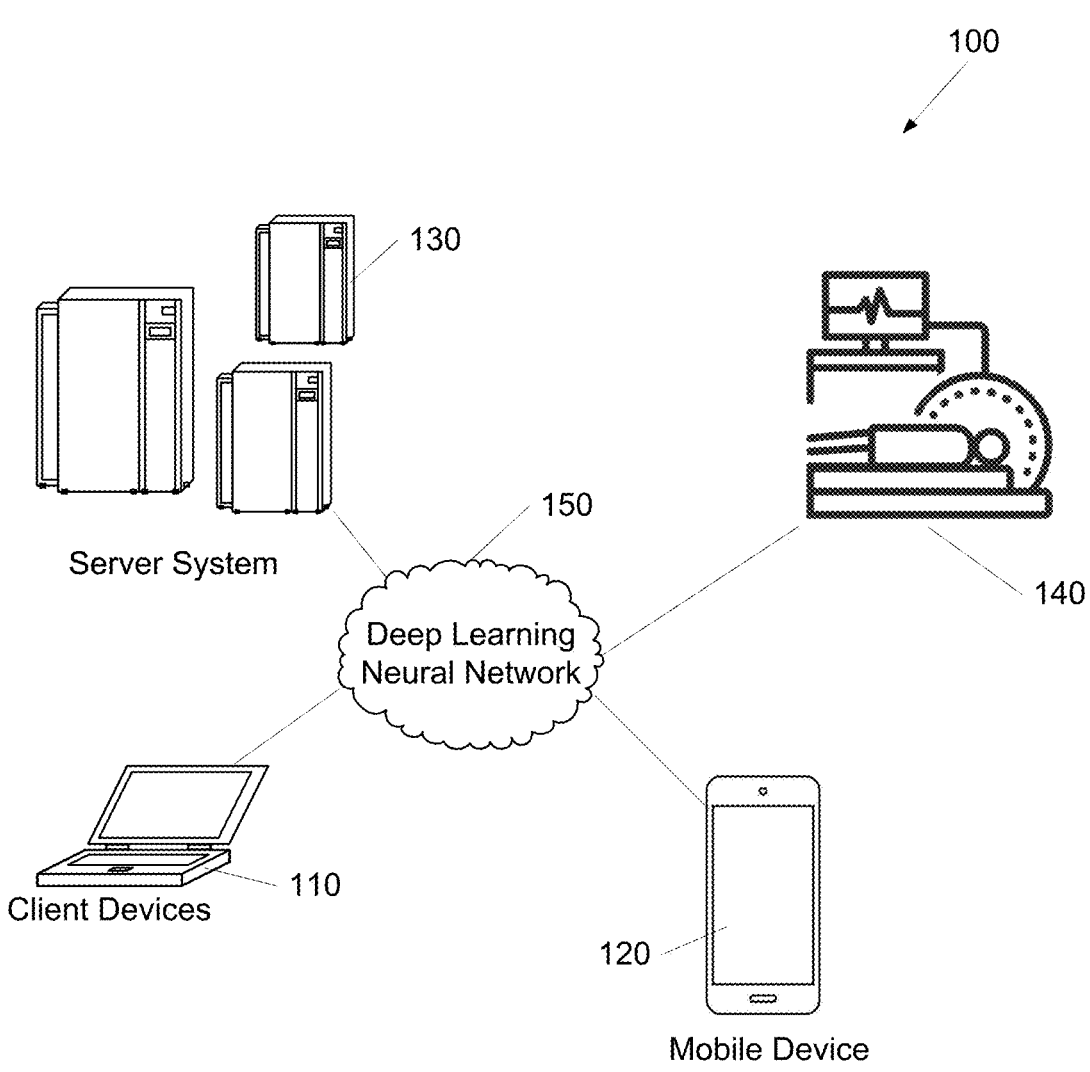
FIG. 1 illustrates an example of a deep learning neural network architecture in which one or more aspects described herein may be implemented.

The following detailed description illustrates embodiments of the present disclosure and ways in which they can be implemented. Although some modes of carrying out the present disclosure have been disclosed, those skilled in the art would recognize that other embodiments for carrying out or practicing the present disclosure are also possible.

The disclosed subject matter may be further described using definitions and terminology as follows. The definitions and terminology used herein are for the purpose of describing particular embodiments only, and are not intended to be limiting.

As used in this specification and the claims, the singular forms "a," "an," and "the" include plural forms unless the context clearly dictates otherwise. For example, the term "patient" should be interpreted to mean "one or more patients" and unless the context clearly dictates otherwise. As used herein, the term "plurality" means "two or more."

As used herein, "about", "approximately," "substantially," and "significantly" will be understood by persons of ordinary skill in the art and will vary to some extent on the context in which they are used. If there are uses of the term that are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

The phrase "such as" should be interpreted as "for example, including." Moreover, the use of any and all exemplary language, including but not limited to "such as", is intended merely to better illuminate the invention and does not pose a limitation on the scope of the invention unless otherwise claimed.

Furthermore, in those instances where a convention analogous to "at least one of A, B and C, etc." is used, in general such a construction is intended in the sense of one having ordinary skill in the art would understand the convention (e.g., "a system having at least one of A, B and C" would include but not be limited to systems that have A alone, B alone, C alone, A and B together, A and C together, B and C together, and/or A, B, and C together.). It will be further understood by those within the art that virtually any disjunctive word and/or phrase presenting two or more alternative terms, whether in the description or figures, should be understood to contemplate the possibilities of including one of the terms, either of the terms, or both terms. For example, the phrase "A or B" will be understood to include the possibilities of "A" or 'B or "A and B."

All language such as "up to," "at least," "greater than," "less than," and the like, include the number recited and refer to ranges which can subsequently be broken down into subranges as discussed above.

A range includes each individual member. Thus, for example, a group having 1-3 members refers to groups having 1, 2, or 3 members. Similarly, a group having 6 members refers to groups having 1, 2, 3, 4, or 6 members, and so forth.

The modal verb "may" refers to the preferred use or selection of one or more options or choices among the several described embodiments or features contained within the same. Where no options or choices are disclosed regarding a particular embodiment or feature contained in the same, the modal verb "may" refers to an affirmative act regarding how to make or use and aspect of a described embodiment or feature contained in the same, or a definitive decision to use a specific skill regarding a described embodiment or feature contained in the same. In this latter context, the modal verb "may" has the same meaning and connotation as the auxiliary verb "can."

In the present disclosure, the terms "patient," "subject," and "individual" may refer to a human or non-human being. The terms "patient," "subject," and "individual" may be used interchangeably throughout the present disclosure.

In the present disclosure, the terms "real-time" and "near real-time" may refer to processing that requires a continual input, constant processing, and steady output of data which may occur over the course of seconds or milliseconds, fractions of seconds, or minutes. The terms "real-time" and "near real-time" may be used interchangeably throughout the present disclosure.

Catheter angiography is a minimally invasive imaging technique that allows physicians to visualize vascular disorders with unrivalled spatial and temporal resolution. Catheter angiography remains the gold standard for the diagnosis and characterization of many vascular disorders, and it provides the foundation for endovascular interventions to treat numerous devastating pathologies, including stroke, cerebral aneurysms, arteriovenous malformations, and myocardial infarctions.

Catheter angiography is performed by inserting a small catheter into the arteries of the body, injecting iodinated contrast through the catheter, and recording a series of fluoroscopic images as the contrast traverses the vasculature. However, superimposed fluoroscopic densities from the bone and soft tissues obscure evaluation of the vessels. For decades, angiographers have utilized DSA to better visualize the vasculature. In this technique, a fluoroscopic image mask is acquired prior to contrast injection, and the mask is subsequently subtracted from image frames recorded after contrast injection. In ideal conditions, DSA will provide an image of the vessels alone, unobscured by superimposed bone and soft tissue densities. This concept has been further extended to 3D rotational angiography, in which a full 3D acquisition is obtained before and after contrast injection to improve visualization of the vasculature.

DSA, however, is heavily affected by motion that occurs between the acquisition of the mask frame and subsequent images. Thus, voluntary, respiratory, or cardiac motion can all degrade vascular imaging with the Digital Subtraction technique. Furthermore, the acquisition of a mask frame increases radiation exposure to the patient and staff, particularly during rotational angiography, which requires many X-ray projections to compute 3D reconstructions, substantially increasing the radiation dose.

The deep learning algorithm disclosed herein can perform both vessel segmentation and computational isolation of vascular contrast enhancement on raw angiographic images to mitigate or overcome the degrading effects of motion and to minimize the radiation dose.

Deep learning is a class of machine learning that utilizes many-layered neural networks to approximate complex nonlinear mathematical functions and to solve difficult problems that may not otherwise be mathematically tractable. The past decade has shown remarkable growth in the application of deep learning with convolutional neural networks to visual tasks, including object recognition/labeling, localization, and segmentation. Recent advances have been propelled by the development of new mathematical techniques for network training such as back-propagation, regularization, and drop-out, and by the decreasing cost of powerful, massively parallel, graphics processing units that enable network training. Additionally, open source software, including PyTorch, TensorFlow, and Keras, has democratized deep learning and markedly accelerated the application of these technologies into subspecialty fields. Today, with the ready availability of these deep learning technologies, the greatest barrier to algorithm development is often the acquisition of a suitable dataset for supervised, semi-supervised, or unsupervised learning.

To train a system to perform vessel segmentation and isolate vascular enhancement, historical raw/native unsubtracted angiographic images are mapped to historical DSA subtracted images, without the need for a pre-contrast injection digital mask. The novel algorithm disclosed herein generates an artificial subtraction angiogram from the raw images of the angiographic series, using a user-defined number of sequential angiographic images used as input to the neural network. Image segmentation is a common task in the machine learning community. A standard U-Net architecture is the most effective way at this time to perform image segmentation. The output layer of a standard U-Net is a pixel-wise sigmoid or softmax activation function that provides a probability, between zero and one, reflecting the network's understanding that a selected pixel belongs to a certain class, for example, a blood vessel. Typically, the probability is rounded to obtain the final segmentation mask. Ultimately, the segmentation mask is binary (i.e., zero belonging to background and one belonging to the structure of interest). Accordingly, a vascular mask may subsequently be generated in accordance with the systems and methods disclosed herein.

The neural network disclosed herein is a modification of a 3D U-Net architecture. The modified 3D U-Net architectures disclosed herein are utilized for image to image regression and/or isolation of vascular enhancement, and perform a per-voxel regression task. Isolated vascular enhancement is an image regression task having a dense image regression neural output. The modified U-Net architectures disclosed herein replace the sigmoid and/or softmax output layer with a linear output layer that enables floating point output values directly predicting the X-ray densities attributed to vascular contrast enhancement. The algorithm replaces the last several layers of a 3D U-Net with image regression layers that are trained to predict the per-voxel continuous variable X-ray densities of the subtraction angiogram, thus performing an artificial subtraction image regression task. The output of the neural network predicts the X-ray densities over the entire image space. The neural network learns to predict the X-ray densities based upon the training dataset. Bone and soft tissue have recognizable characteristics (both temporal and spatial) that can be identified by the image-to-image regression that are subsequently removed from the output image. This unique technique provides an artificial subtraction of the bone and soft tissue, directly computationally isolating the vascular density resulting in the generation of vastly improved angiogram images.

For example, conventional fluoroscopic angiography machines are used to capture 2D images of the body, and many frames of these 2D images may be collected over time. Importantly, according to the methods disclosed herein, the extracted subset of the 2D images may be stacked to create a 3D reconstruction that may include 1) a height of image; 2) a width of image; and 3) a number of frames. As such, the 3D reconstruction may be characterized as a video or filmstrip. Such a method is a radical differentiation from other known approaches that train models based on many independent 2D angiographic images that only include 1) a height of image; and 2) a width of image, without considering all the frames of the sequence as a collective whole along the time dimension. Further, such a technique is distinct from other conventional approaches (e.g., CT) that independently use 3D volumetric images that only include 1) a height of image; 2) a width of image; and 3) a depth of image. A subset of angiograms in which the patient motion is small is identified and extracted from the collection of images. Digital subtraction angiography, which performs well in the motion-free setting is then computed on this subset of angiograms in which the patient motion is small. Artificial motion is applied to the input raw and DSA data pairs from the subset of angiograms in which patient motion is small by computationally "moving" the images from frame to frame. By utilizing the 3D angiographic reconstructions, both translational and rotational motions can be introduced. Deep learning will then be performed, in which the network will be trained using the "motion-enhanced" raw dataset as input, and the "motion-enhanced" DSA images as the target output. After completion of this step, the algorithm will result in both a reduced radiation dose and improved image quality when compared to traditional DSA.

FIG. 1 illustrates an operating environment 100 in accordance with an embodiment of the invention. The operating environment 100 includes at least one client device 110, and/or at least one mobile device 120, and/or at least one server system 130, and at least one angiographic system 140 in communication via a deep learning neural network 150. It will be appreciated that the network connections shown are illustrative and any means of establishing a communications link between the computers may be used. The existence of any of various network protocols such as TCP/IP, Ethernet, FTP, HTTP and the like, and of various wireless communication technologies such as GSM, CDMA, WiFi, and LTE, is presumed, and the various computing devices described herein may be configured to communicate using any of these network protocols or technologies. Any of the devices and systems described herein may be implemented, in whole or in part, using one or more computing devices described with respect to FIG. 2.

Client devices 110 and/or mobile device 120 may provide user interface requests to the server system 130, and/or the angiographic system 140, and/or the deep learning neural network 150 as described herein. The network 150 may include a local area network (LAN), a wide area network (WAN), a wireless telecommunications network, and/or any other communication network or combination thereof.

Some or all of the data described herein may be stored using any of a variety of data storage mechanisms, such as databases. These databases may include, but are not limited to relational databases, hierarchical databases, distributed databases, in-memory databases, flat file databases, XML databases, NoSQL databases, graph databases, and/or a combination thereof. The data transferred to and from various computing devices in the operating environment 100 may include secure and sensitive data, such as confidential documents, customer personally identifiable information, and account data. It may be desirable to protect transmissions of such data using secure network protocols and encryption and/or to protect the integrity of the data when stored on the various computing devices. For example, a file-based integration scheme or a service-based integration scheme may be utilized for transmitting data between the various computing devices. Data may be transmitted using various network communication protocols. Secure data transmission protocols and/or encryption may be used in file transfers to protect the integrity of the data, for example, File Transfer Protocol (FTP), Secure File Transfer Protocol (SFTP), and/or Pretty Good Privacy (PGP) encryption. In many embodiments, one or more web services may be implemented within the various computing or mobile devices. Web services may be accessed by authorized external devices and users to support input, extraction, and manipulation of data between the various computing devices in the operating environment 100. Web services built to support a personalized display system may be cross-domain and/or cross-platform, and may be built for enterprise use. Data may be transmitted using the Secure Sockets Layer (SSL) or Transport Layer Security (TLS) protocol to provide secure connections between the computing devices. Web services may be implemented using the WS-Security standard, providing for secure SOAP messages using XML encryption. Specialized hardware may be used to provide secure web services. For example, secure network appliances may include built-in features such as hardware-accelerated SSL and HTTPS, WS-Security, and/or firewalls. Such specialized hardware may be installed and configured in the operating environment 100 in front of one or more computing or mobile devices such that any external devices may communicate directly with the specialized hardware.

Figure 2:
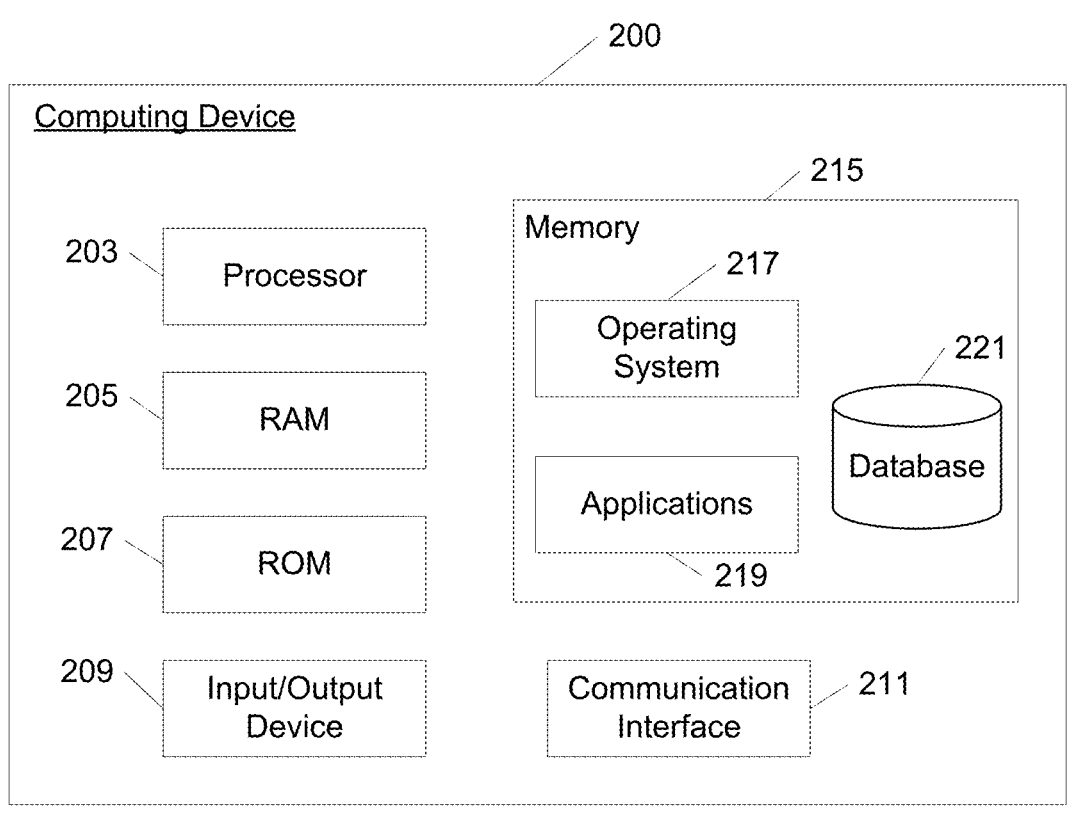
FIG. 2 illustrates an example computing device in accordance with one or more aspects described herein.

Turning now to FIG. 2, a computing device 200 in accordance with an embodiment of the invention is shown. The computing device 200 may include a processor 203 for controlling overall operation of the computing device 200 and its associated components, including RAM 205, ROM 207, input/output device 209, communication interface 211, and/or memory 215. A data bus may interconnect processor(s) 203, RAM 205, ROM 207, memory 215, I/O device 209, and/or communication interface 211. In some embodiments, computing device 200 may represent, be incorporated in, and/or include various devices such as a desktop computer, a computer server, a mobile device, such as a laptop computer, a tablet computer, a smart phone, any other types of mobile computing devices, and the like, and/or any other type of data processing device.

Input/output (I/O) device 209 may include a microphone, keypad, touch screen, and/or stylus through which a user of the computing device 200 may provide input, and may also include one or more of a speaker for providing audio output and a video display device for providing textual, audiovisual, and/or graphical output. Communication interface 211 may include one or more transceivers, digital signal processors, and/or additional circuitry and software for communicating via any network, wired or wireless, using any protocol as described herein. Software may be stored within memory 215 to provide instructions to processor 203 allowing computing device 200 to perform various actions. For example, memory 215 may store software used by the computing device 200, such as an operating system 217, application programs 219, and/or an associated internal database 221. The various hardware memory units in memory 215 may include volatile and nonvolatile, removable and non-removable media implemented in any method or technology for storage of information such as computer-readable instructions, data structures, program modules, or other data. Memory 215 may include one or more physical persistent memory devices and/or one or more non-persistent memory devices. Memory 215 may include, but is not limited to, random access memory (RAM) 205, read only memory (ROM) 207, electronically erasable programmable read only memory (EEPROM), flash memory or other memory technology, optical disk storage, magnetic cassettes, magnetic tape, magnetic disk storage or other magnetic storage devices, or any other medium that may be used to store the desired information and that may be accessed by processor 203.

Processor 203 may include a single central processing unit (CPU), which may be a single-core or multi-core processor, or may include multiple CPUs. Processor(s) 203 and associated components may allow the computing device 200 to execute a series of computer-readable instructions to perform some or all of the processes described herein. Although not shown in FIG. 2, various elements within memory 215 or other components in computing device 200, may include one or more caches, for example, CPU caches used by the processor 203, page caches used by the operating system 217, disk caches of a hard drive, and/or database caches used to cache content from database 221. For embodiments including a CPU cache, the CPU cache may be used by one or more processors 203 to reduce memory latency and access time. A processor 203 may retrieve data from or write data to the CPU cache rather than reading/writing to memory 215, which may improve the speed of these operations. In some examples, a database cache may be created in which certain data from a database 221 is cached in a separate smaller database in a memory separate from the database, such as in RAM 205 or on a separate computing device. For instance, in a multi-tiered application, a database cache on an application server may reduce data retrieval and data manipulation time by not needing to communicate over a network with a back-end database server. These types of caches and others may be included in various embodiments, and may provide potential advantages in certain implementations of devices, systems, and methods described herein, such as faster response times and less dependence on network conditions when transmitting and receiving data.

Although various components of computing device 200 are described separately, functionality of the various components may be combined and/or performed by a single component and/or multiple computing devices in communication without departing from the invention.

Figure 3:
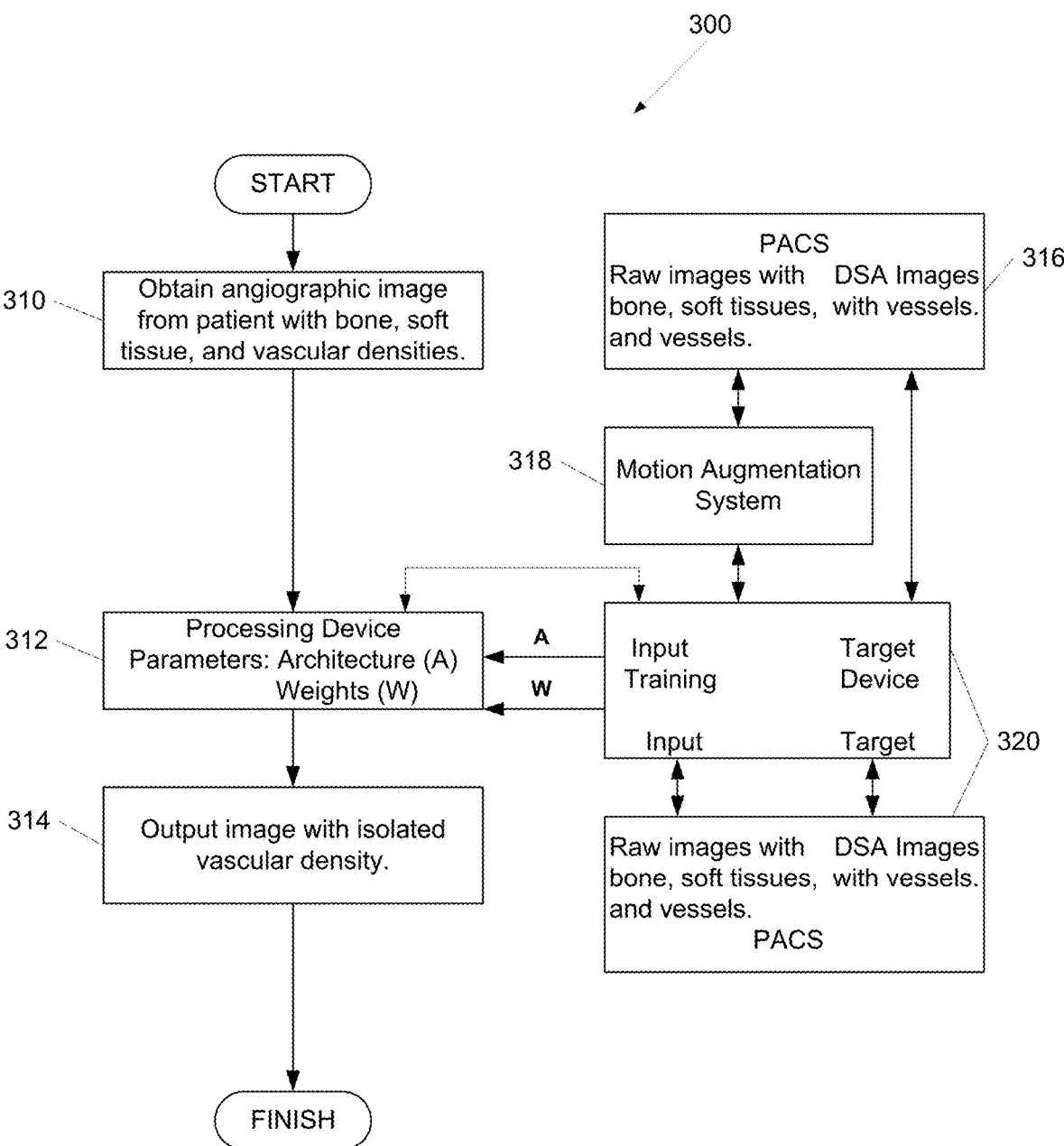
FIG. 3 depicts a conceptual diagram of a maskless subtraction angiography flow using a neural network according to one or more aspects of the disclosure described herein.

FIG. 3 depicts a conceptual diagram of a maskless subtraction angiography flow using a neural network according to one or more aspects of the disclosure. In step 310, an angiographic image is obtained from a patient or individual. According to step 316, a set of data is obtained from the neural network and may be extracted from historical angiogram data. In certain examples, the data includes identified motion from the historical angiogram. At step 318, artificial motion is generated based upon the set of data and the obtained angiographic image. At step 320, model training and optimization is performed using motion-augmented data created in step 318. At step 312, a final angiographic image is generated in which bone and soft tissue densities are removed, and isolated vascular densities are present. This final angiographic image in step 314 can be generated with high image quality even in the setting of substantial patient motion.

Figure 4:
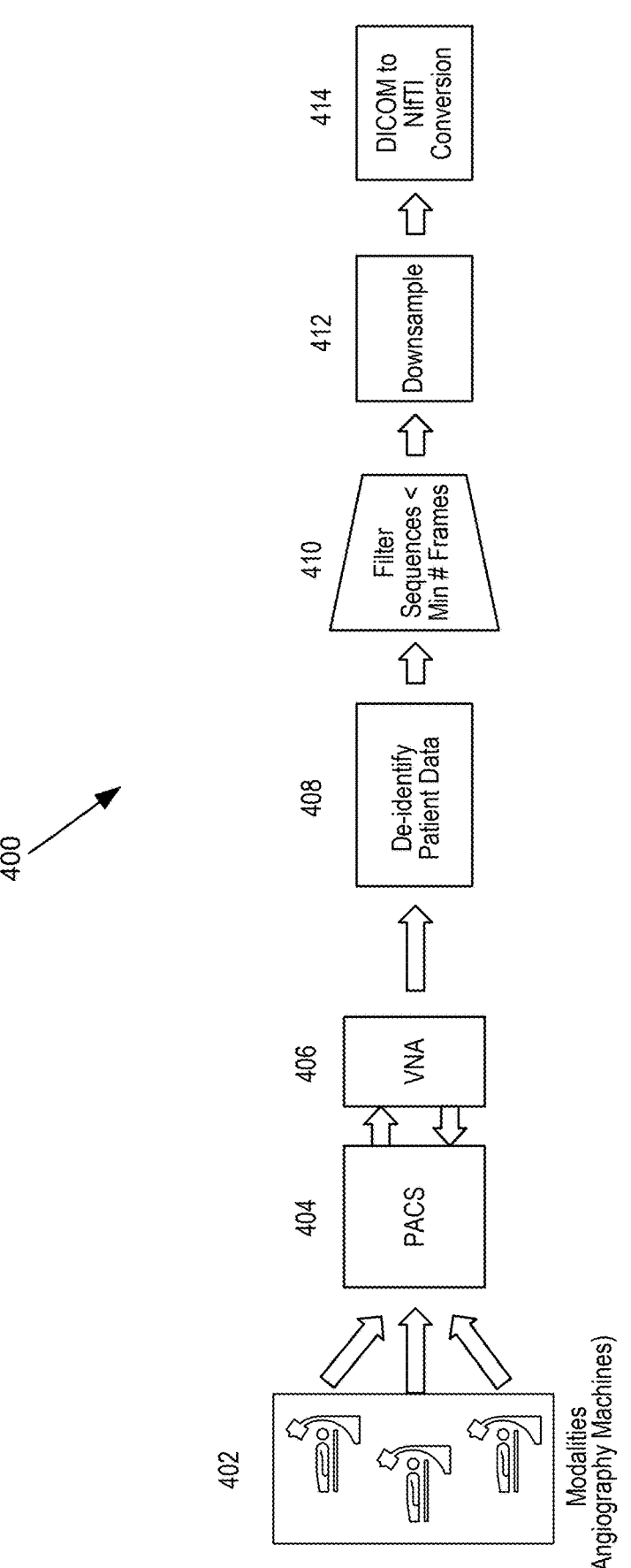
FIG. 4 depicts a maskless artificial subtraction angiography workflow diagram for data pre-processing of collected historical angiographic datasets through all modalities according to one or more aspects of the disclosure described herein.

FIG. 4 depicts a maskless artificial subtraction angiography workflow diagram for data/image pre-processing 400 of collected historical angiographic datasets from various angiographic devices. Example angiographic devices may include 3D rotational angiographic imaging devices, MRI devices, CT devices, X-ray devices, etc. According to step 402, angiographic data or inputs (e.g., imaging) may be collected. Collected angiographic inputs may include 2D images as well as 3D images consisting of two spatial dimensions and one temporal dimension. The inputs may then be converted to 3D, spatiotemporal, and multi-frame images that provide superior artificial digital subtraction angiography images over conventional 2D/3D images according to the methods and systems disclosed herein. Conventional 2D/3D spatial, single-frame angiographic inputs, however, may be collected and processed according to the methods disclosed herein despite inferior image generation. The data from all modalities may be input to the picture archiving and communication system (PACS) at step 404 and transmitted to a Vendor Neutral Archive (VNA) at step 406. At step 408, patient data may be removed from the collected angiographic data. At step 410, image sequences may be filtered to ensure a proper number of acceptable images are present across a predetermined number of frames.

A required number of image frame data may be at least, or between about 2 to about 32 frames/series. According to step 412 of FIG. 4, the data may be downsampled to reduce file size in some instances. At step 414, the processed data may be converted from Digital Imaging and Communications in Medicine (DICOM) images to Neuroimaging Informatics Technology Initiative (NIFTI) file format, or the pixel data may be otherwise extracted. In some examples, the processed data may include three-dimensional, spatiotemporal information from at least 10,000 historical angiographic datasets. One or more steps of the example method of FIG. 4 may be rearranged (e.g., performed, sent, or received in a different order), omitted, and/or otherwise modified, and/or other steps and/or processing added.

The motion augmentation algorithm disclosed herein may harvest randomly sampled motion data from the dataset collected and described above and depicted in FIG. 4. The randomly sampled data is ultimately processed to calculate an artificial motion estimate to generate a training dataset for the described matching learning model, which may create an image with bone structures removed from raw angiographic images collected from a patient in real-time. A Feature-Based Motion Estimation pipeline using classic computer vision techniques may be applied to estimate motion from the database of angiographic data collected in the process described in FIG. 4. In addition, the motion estimates may be used in the step of training a neural network. Motion-free datasets can be used to compute digital subtraction angiograms of high quality. The motion estimates derived in FIG. 6 can be applied to the motion-free raw angiograms and their corresponding high-quality digital subtraction angiograms to create corresponding motion-augmented raw angiography—subtraction angiography data pairs. The resulting data pairs may be utilized as input-output data pairs for training and optimizing the system that generates maskless artificial subtraction angiography images in the setting of motion.

Figure 5:
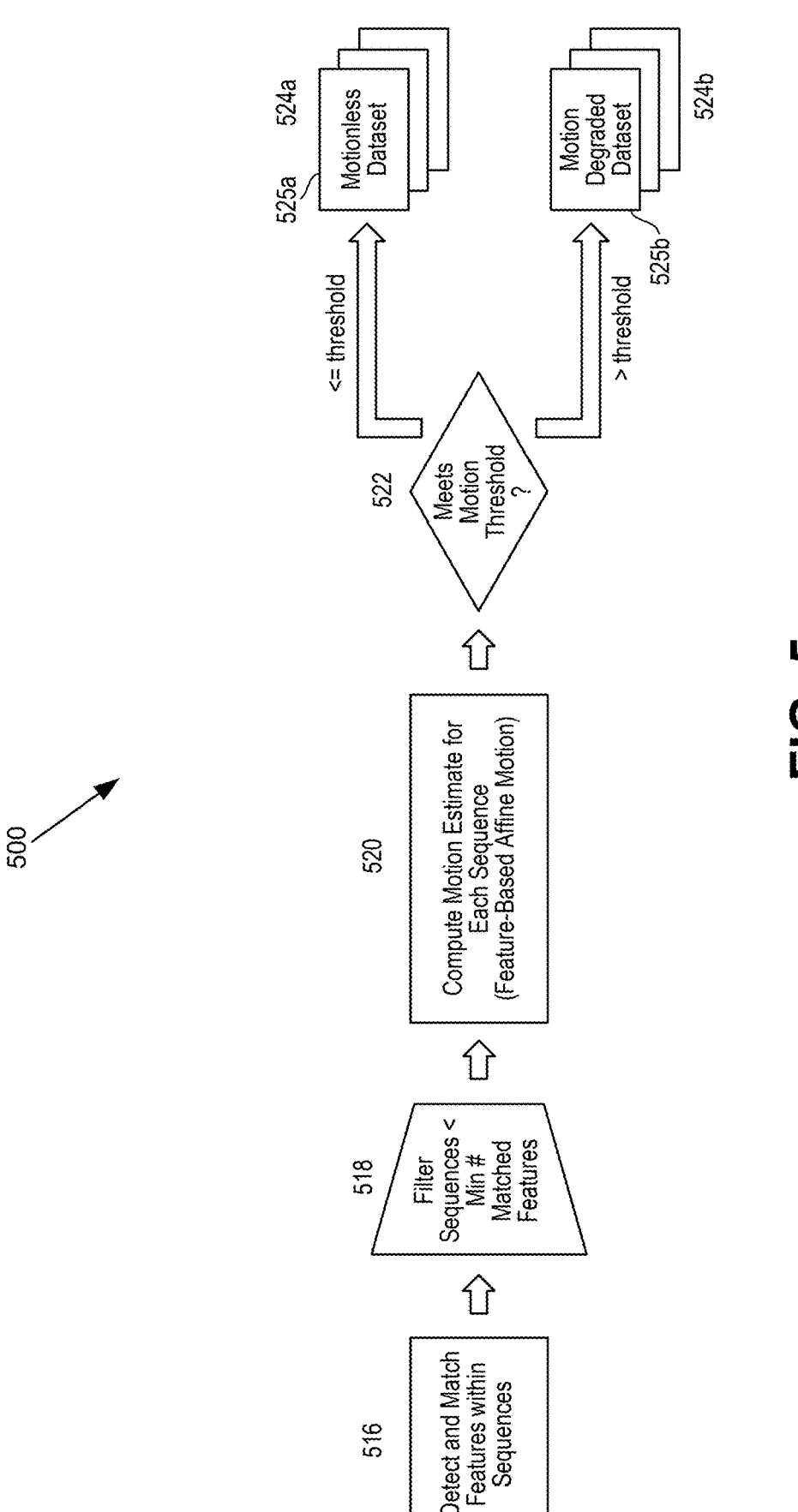
FIG. 5 depicts a maskless artificial subtraction angiography workflow diagram for the motion categorization of the processed historical data generated in the workflow diagram of FIG. 4 according to one or more aspects of the disclosure described herein.

FIG. 5 depicts the workflow diagram for the motion categorization 500 of the processed historical data generated in the workflow diagram of FIG. 4. According to step 516, the final processed data from step 414 in FIG. 4 may be further processed to detect and match features within the sequence of images. For example, known anatomical features (such as skull orbit shape, circumference, geometry; mandible shape, size, geometry; tibia length, thickness, geometry; etc.) may be identified and matched within the sequences of processed angiographic data. At step 518, matched sequence data may be filtered out of the dataset if a minimum number of matched features and number of matched sequences are not achieved. A required number of image frame data or sequences may be at least 8, or between about 2 to about 32 frames/sequences. According to step 520, a motion estimate for each sequence may be computed using the Feature-Based Motion Estimation pipeline. Upon meeting a required motion threshold at step 522, the data may be separated at step 524*a* and step 524*b* into a motion-free (i.e., motionless) dataset 525*a* and a motion-degraded dataset 525*b*. One or more steps of the example method of FIG. 5 may be rearranged (e.g., performed, sent, or received in a different order), omitted, and/or otherwise modified, and/or other steps and/or processing added.

Figure 6:
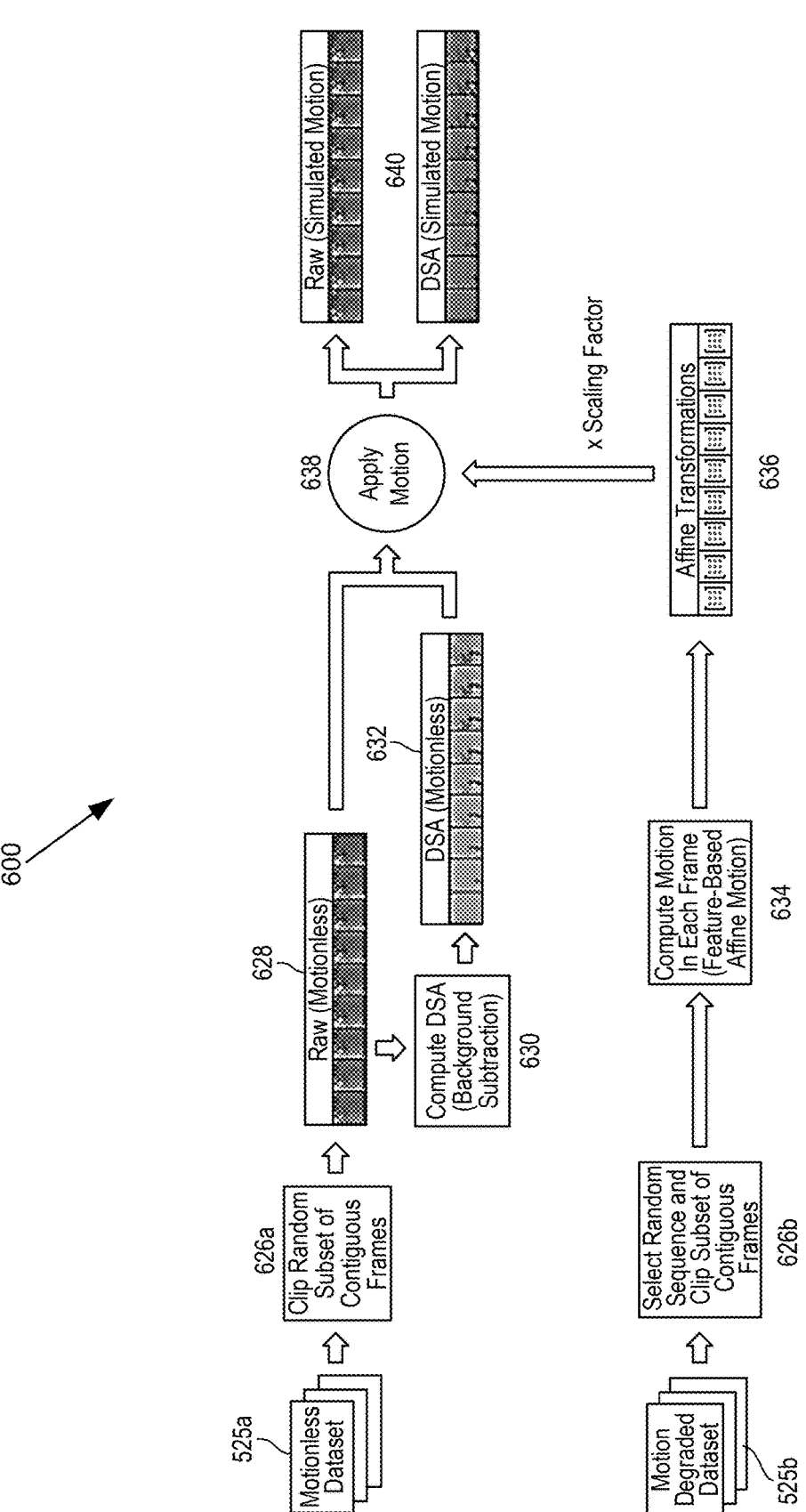
FIG. 6 depicts a maskless artificial subtraction angiography workflow diagram for the calculation of motion augmentation and application of an artificial motion/motion estimate to the motion categorization datasets generated in the workflow diagram of FIG. 5 according to one or more aspects of the disclosure described herein.

FIG. 6 depicts the workflow diagram for the calculation of predicted motion estimates and application of the predicted motion 600 to the motion categorization datasets 525*a* and 525*b*. At steps 626*a* and 626*b*, a random sample of the motion-free dataset 525*a* is selected, and a random sample of the motion-degraded dataset 525*b* is selected. The random motion-degraded dataset includes known and matched anatomic features that can be used to measure interframe motion. At step 630, the background is subtracted from the motionless raw dataset 628 (raw motionless/low-motion angiographic data) to generate a motionless digital subtraction angiogram 632. The measured interframe motion from the randomly sampled motion-degraded dataset is applied to the motionless dataset to obtain the high-quality input raw angiography-output digital subtraction angiography data pairs that may be utilized for training and optimizing the system for generation of the maskless artificial subtraction angiography images. In other examples, the interframe motion may be further augmented with additional artificial motion data or real motion data prior to application to the motionless dataset for the generation of a motion-augmented data pair. At step 634, the random sample of the motion-degraded dataset 525*b* is used to compute the motion in each frame using the Feature-Based Affine Motion technique. From this computation, a motion estimate is calculated. At step 636, a scaling factor is optionally applied to the calculated artificial motion. At step 638, the calculated motion estimate is applied to the motionless digital subtraction angiography 632 to generate a final angiographic image 640 with bone structures removed from the final angiographic image, leaving only vascular structures visible. This same calculated motion estimate is applied to the motionless raw angiogram 628 so that the raw angiogram 628 and the subtraction angiogram 632 are both augmented with the same motion time series. Said differently, a known and realistic amount of predicted motion may be injected into the raw angiogram and subtraction angiogram of the randomly selected motion-free dataset in order to generate appropriate input-output data pairs 640 for training the algorithm disclosed herein. One or more steps of the example method of FIG. 5 may be rearranged (e.g., performed, sent, or received in a different order), omitted, and/or otherwise modified, and/or other steps and/or processing added.

Example 1

Imaging Data Preprocessing.

All angiographic studies acquired by neuro interventionalists at Northwestern Memorial Hospital in 2019 were downloaded from the Vendor Neutral Archive. A total of 516 angiographic studies were collected from 404 unique patients between Jan. 1, 2019 and Dec. 31, 2019, including the start and end dates. No exams were excluded. This set of angiographic studies was then divided into training and test sets, ensuring that no patients were present in both groups to prevent the leakage of anatomic information across sets. 323 patients (~80%) with 404 studies (~78%) were assigned to the training set, and 81 patients (~20%) with 112 studies (~22%) were assigned to the test set. From these data, 6812 native angiographic series were identified in the training set, and 1972 native angiographic series from the test set.

The DICOM images were converted into NIFTI file format and de-identified. A coded identifier list was retained on a local, encrypted hard drive, which linked the patient identification and the study Accession Number to a randomly generated hash label, which was generated during the de-identification process. During NIFTI conversion, images were downsampled from native 1024×1024 pixels to 512×512 pixels with bicubic interpolation over a 4×4 pixel neighborhood using the OpenCV resize function. Pixel gray values were encoded in native DICOM and converted NIFTI formats using 12 bits, with values from 0 to 4094. Acquisitions ranged from 1 to 6 frames per second. Angiographic series with fewer than 16 frames were discarded, leaving 5798 series in the training group and 1638 series in the test group.

From each of angiographic series, a heuristic, feature-based method was used to identify matching image features (i.e., anatomical features) across all angiographic frames, and then to estimate the affine transformation from all frames of the series back onto the base frame. To strengthen the feature-based affine motion estimate, a series in which fewer than 100 matching image features were discovered were excluded, leaving 5045 series in the training group and 1042 in the test group. Using the derived motion estimates, the datasets were then divided by the degree of measured motion. Angiograms with less than a single pixel of maximal translational deviation from the base frame, as measured by the feature-based motion estimate, were considered to be "motionless" or "motion-free" (i.e., 2468 series in the training set and 713 in the test set), and angiograms with more than this threshold of motion, were considered to be "motion-degraded" (i.e., 2577 in the training set and 689 in the test set). Surprisingly, it was observed that even small amounts of motion could create substantial subtraction artifact when the vascular densities were superimposed on complex osseous backgrounds.

A motion-augmented hold-out test set was then created. For each "motionless" angiogram in the test set, a random subset of 16 contiguous frames was selected, the pixel intensities were converted to floating point and scaled to the range of [0,1], and a digital subtraction angiogram (DSA) was computed on these stationary frames. A random angiogram was then selected from the "motion-degraded" test set, a random subset was chosen from the 16 contiguous frames from the associated affine transformations generated using feature-based motion estimation, the translational components of these affine transformations was scaled by a random uniform value selected on the range [0.5, 2.0], and then these affine transformations were applied to the 16 contiguous raw and DSA "motionless" frames. Following these steps, motion-augmented raw input angiograms were generated with paired motion-augmented "ground-truth" DSA. These same pre-processing steps were followed to generate training and validation datasets.

3D Spatiotemporal Neural Network

A 3D UNet was trained with the motion-augmented data pairs generated following the steps described above. The 3D UNet was constructed to take a motion-augmented raw angiogram as input and to generate an output that represents a motion-augmented subtraction angiogram in which the bone and soft tissue densities are removed. Traditional UNets utilize softmax outputs for image segmentation tasks. In our example, we exchanged the softmax output layer for a linear regression output layer that allowed the UNet to directly estimate the isolated vascular densities of the angiograms. The 3D UNet was created in a way that allowed it to receive spatiotemporal angiographic inputs of variable temporal frame length. Deep supervision layers were incorporated into the 3D UNet architecture to optimize training. A Mean Squared Error loss function was utilized to minimize the difference between the 3D UNet output and the target motion-augmented subtraction angiogram during training.

Feature-Based Motion Estimation.

A first order estimate of frame-by-frame angiographic motion was generated using a heuristic, feature-based approach. Within each series, image features were identified in each frame using the OpenCV ORB (Oriented FAST and Rotated BRIEF) algorithm. Image features from the first frame of each angiographic sequence were then matched to those identified in all subsequent frames of the series. Feature matching was performed with the Flann Based Matcher using default parameters detailed by OpenCV documentation. Proposed matches were then retained only if the ratio of the distance to the closest neighbor in feature/descriptor space to the distance to the second closest was less than 0.7, following OpenCV documentation and the strategy initially described by David G. Lowe, "Distinctive image features from scale-invariant keypoints," International Journal of Computer Vision, 60, 2 (2004), pp. 91-110, incorporated herein by reference in its entirety, for all uses and purposes. These matching image features were then utilized to estimate affine transformation matrices using the OpenCV RANSAC algorithm. In this way, for each angiographic series, a set of affine transformation matrices was then generated that mapped each frame in the series back onto the first frame:

$$\{A_{i1}\}^{i=1 \dots F} = \{A_{11}, A_{21}, A_{31}, \dots, A_{F1}\},$$

where F represents the number of frames in the series, and the affine transformation matrix Ai1 represents the matrix that maps the ith frame onto the 1st (base) frame.

The model disclosed herein estimates motion between frames, and does not attempt to correct for the frame rate. This strategy was chosen because it has the desired effect of introducing a larger range of temporal frequencies into the motion-augmented training dataset.

Constraints.

Generally, the deep learning algorithm may be constrained by the degree to which the training dataset reflects the prediction dataset. It is anticipated that the algorithm could perform optimally at alternate institutions if provided with additional training data from those institutions and environments.

This research was designed primarily to evaluate the impact of temporal information on vascular density isolation utilizing deep neural networks. To maximize the number of temporal frames that could be used as neural network input within GPU memory constraints, the spatial dimensions of the native angiographic images was downsampled from 1024×1024 to 512×512. New generations of deep learning hardware will enable future work to be performed at native spatial resolutions.

Even in angiographic series of the rigid skull, planar motion can be extremely complex due to the interplay of 3D translation, 3D rotation about an unknown center, and the projection of these 3D transformations onto a 2D plane. Furthermore, neuroangiographic series of the face, neck, or spine may introduce the additional complexity of nonrigid biological motion at joints in the axial skeleton and mandible. The current motion model is a first order approximation based on the clinical observation that most motion in neuroangiographic studies is translational. Even with this first order approximation, the deep learning approach disclosed herein has achieved surprising and unexpected results. Future work may integrate more complex models of motion.

Results.

Utilizing the 3D spatiotemporal inputs for artificial subtraction angiography disclosed herein yields surprising and unexpected improvements in image quality. In prior art utilizing conventional 2D spatial inputs, see Gao, Y., Song, Y., Yin, X. et al. Deep learning-based digital subtraction angiography image generation. *Int J CARS* 14, 1775-1784 (2019), reported Mean Squared Error was on the order of 0.15 on test sets. In the systems and methods disclosed herein, when utilizing 3D spatiotemporal input with 16 temporal frames of similar input data statistics (mean and standard deviation), a Mean Squared Error of approximately 0.003 was achieved—a remarkable improvement. Additionally, when using similarity metrics (SSIM), Gao et al only reported values of approximately 0.88 with 2D spatial inputs compared to SSIM values of approximately 0.97 achieved with the systems and methods disclosed herein.

Figures 7A, 7B, 7C:
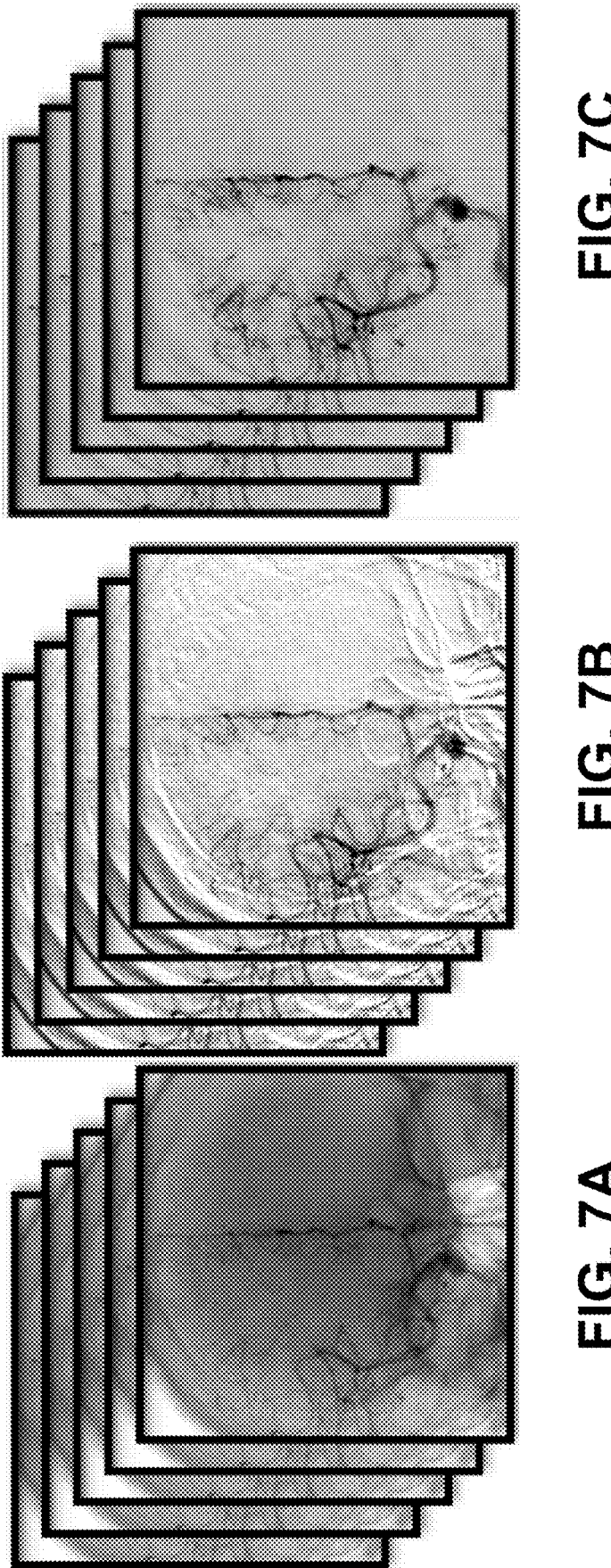
FIG. 7A is a raw angiographic image with vascular contrast, bone, and soft tissue densities visible.
FIG. 7B is an image of a conventional digital subtraction angiogram degraded by motion artifacts in the skull base.
FIG. 7C is an artificial digital subtraction angiography image generated using a deep learning neural network, in real-time, according to one or more aspects of the disclosure described herein.

As shown in FIG. 7A, raw angiographic images with vascular contrast include visible bone and soft tissue densities. The bone structures and soft tissue obstruct the vascular structures of interest. FIG. 7B is an image of a conventional digital subtraction angiogram degraded by motion artifacts in the skull base. Bone structures are still present and remain visible in FIG. 7B. An example artificial digital subtraction angiography image generated in real-time or near real-time, using the machine learning model disclosed herein, is shown in FIG. 7C. The bone and soft tissue structures are removed from the final angiographic image, and a clear image of the isolated vascular densities is visible in FIG. 7C.

In the foregoing description, it will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations that are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

We claim:

1. A method of generating a maskless artificial subtraction angiography image using a machine learning model comprising:

obtaining raw angiographic images from an individual, wherein the raw angiographic images are three-dimensional, spatiotemporal, multi-frame angiographic inputs;

utilizing spatial and temporal information in the raw angiographic images to identify vascular densities; and generating a final three-dimensional spatiotemporal angiographic image, wherein bone and soft tissue structures are removed from the final angiographic image, leaving isolated vascular densities, wherein a method for training and optimizing the method of generating the maskless artificial subtraction angiography image using the machine learning model further comprises the steps of:

obtaining a database of raw angiographic images from a plurality of individuals, wherein the raw angiographic images are three-dimensional, spatiotemporal, multi-frame angiographic inputs;

calculating motion estimates using the database of raw angiographic images;

isolating motionless angiographic images from the database;

transforming the motionless raw angiographic images into digital subtraction angiography images to generate input-output data pairs;

applying the motion estimates to the input-output data pairs; and utilizing the data pairs for training and optimizing the generation of the maskless artificial subtraction angiography image.

2. The method of claim 1, wherein the final angiographic image is generated in real-time or near real-time.

3. The method of claim 1, wherein raw angiographic images are obtained at a rate of at least 16 frames per second.

4. The method of claim 1, wherein the spatiotemporal data pairs are augmented with motion.

5. The method of claim 1, further comprising the use of augmented motion data or artificial motion data.

6. The method of claim 1, further comprising identifying a plurality of known anatomical features in the raw angiographic images from at least one individual.

7. The method of claim 6, further comprising matching the plurality of known anatomical features in a historical motion-degraded dataset to compute an interframe motion, wherein the motion estimates include the interframe motion, and applying the interframe motion to the motionless angiographic images to obtain high quality input raw angiography-output digital subtraction angiography data pairs.

8. The method of claim 7, wherein the interframe motion is further augmented with additional artificial motion prior to application to the motionless angiographic images for the generation of a motion-augmented data pair.

9. The method of claim 1, wherein the raw angiographic images are obtained from a head or neck of the individual, a torso of the individual, or an appendage of the individual.

10. The method of claim 1, wherein the raw angiographic images are obtained from a three-dimensional rotational angiographic imaging device, MRI device, or CT device, wherein the three-dimensional data consists of three spatial dimensions.

11. A system for generating a maskless artificial subtraction angiography image comprising:

an angiographic imaging device configured to generate raw angiographic images from an individual;

a machine learning model configured to remove bone and soft tissue densities and isolate vascular densities, and wherein the machine learning model is further configured to compute motion estimates, and wherein the motion estimates are generated from a motion-degraded dataset; and a processing device configured to generate a final angiographic image in real-time or near real-time, wherein bone structures are removed from the final angiographic image.

12. The system of claim 11, wherein the raw angiographic images are three-dimensional, spatiotemporal, multi-frame angiographic inputs.

13. The system of claim 11, wherein the machine learning model includes three-dimensional, spatiotemporal information from at least 10,000 historical angiographic datasets.

14. The system of claim 13, wherein the datasets further comprise three-dimensional rotational angiographic imaging device data, MRI device data, or CT device data, wherein the three-dimensional data consists of three spatial dimensions.

15. The system of claim 11, wherein the raw angiographic images comprise a plurality of known anatomic features, wherein the plurality of known anatomic features can be identified on a series of temporal angiographic frames, and wherein the plurality of known anatomic features can be matched across frames to measure interframe motion.

16. The system of claim 11, wherein the raw angiographic images are of a head or neck of the individual, a torso of the individual, or an appendage of the individual.

17. A method of angiographic motion stabilization in artificial subtraction angiography comprising:

collecting a plurality of raw angiographic images, wherein the raw angiographic images are three-dimensional, spatiotemporal, and multi-frame angiographic inputs;

matching known anatomical features from the plurality of raw angiographic images;

computing interframe motion from matched anatomical features;

computing a motion-stabilized series of angiographic images using the computed interframe motion; and generating a digital subtraction angiography from a motion-stabilized dataset, wherein bone structures are removed from a final angiographic image.

18. The method of claim 17, further comprising:

obtaining raw angiographic images from an individual;

matching the known anatomical features of the raw angiographic images from the individual across a series of temporal angiographic frames;

computing a measure of interframe motion using the matched known anatomical features;

generating a motion-stabilized dataset using the interframe motion;

performing digital subtraction angiography on the motion-stabilized series of angiographic images stabilized with the known anatomical features of the raw angiographic images from the individual; and generating a final angiographic image, wherein bone structures are removed from the final angiographic image, and wherein the final angiographic image is generated in real-time or near real-time.

* * * * *